(12) United States Patent
Benson et al.

(10) Patent No.: US 9,468,421 B2
(45) Date of Patent: Oct. 18, 2016

(54) VISUALIZATION OF ASSOCIATED INFORMATION IN ULTRASOUND SHEAR WAVE IMAGING

(75) Inventors: John Benson, Issaquah, WA (US); Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 497 days.

(21) Appl. No.: 13/533,660

(22) Filed: Jun. 26, 2012

(65) Prior Publication Data

US 2013/0218011 A1 Aug. 22, 2013

Related U.S. Application Data

(60) Provisional application No. 61/599,785, filed on Feb. 16, 2012.

(51) Int. Cl.
*A61B 8/08* (2006.01)
*A61B 8/00* (2006.01)

(52) U.S. Cl.
CPC ............ *A61B 8/5223* (2013.01); *A61B 8/463* (2013.01); *A61B 8/485* (2013.01); *A61B 8/461* (2013.01)

(58) Field of Classification Search
CPC .... A61B 8/5223; A61B 8/461; A61B 8/485; A61B 8/463
USPC .......... 600/407, 437–438, 442, 449
See application file for complete search history.

(56) References Cited

U.S. PATENT DOCUMENTS

| | | | |
|---|---|---|---|
| 8,118,744 B2 | 2/2012 | Palmeri et al. | |
| 8,187,187 B2 * | 5/2012 | Fan ........................ | A61B 8/00 600/438 |
| 8,343,050 B2 | 1/2013 | Fan et al. | |
| 2002/0010398 A1 * | 1/2002 | Bonnefous ................... | 600/442 |
| 2005/0283078 A1 * | 12/2005 | Steen ........................ | 600/447 |
| 2006/0285731 A1 | 12/2006 | Jiang et al. | |
| 2007/0049824 A1 * | 3/2007 | Konofagou et al. .......... | 600/437 |
| 2008/0249408 A1 * | 10/2008 | Palmeri et al. ............... | 600/438 |
| 2009/0149751 A1 * | 6/2009 | Mourad et al. ............... | 600/438 |
| 2010/0016718 A1 * | 1/2010 | Fan et al. ...................... | 600/438 |
| 2010/0185085 A1 | 7/2010 | Hamilton et al. | |
| 2010/0241001 A1 | 9/2010 | Palmeri et al. | |
| 2010/0286516 A1 | 11/2010 | Fan et al. | |
| 2013/0066204 A1 * | 3/2013 | Fan ...................... | A61B 8/0858 600/438 |

OTHER PUBLICATIONS

Rebecca C. Boii et al., "Characterization of Cysts using Differential Correlation Coefficient Values from 2D Breast Elastography: Preliminary Study," National Institute of Health, Ultrasound Med Biol, pp. 1-19, Jan. 2008.
L. Chen et al., "A quality-guided displacement tracking algorithm for ultrasonic elasticity imaging," Medical Image Analysis, 13, pp. 286-296, 2009.
U.S. Appl. No. 13/229,408, filed Sep. 9, 2011.
U.S. Appl. No. 13/298,182, filed Nov. 16, 2011.

\* cited by examiner

*Primary Examiner* — Long V Le
*Assistant Examiner* — Colin T Sakamoto

(57) ABSTRACT

Information associated with shear calculation is also displayed in ultrasound shear wave imaging. More information than just a shear wave image is provided for diagnosis. Information about the quality or variables used to determine shear is also displayed. This additional information may assist the user in determining whether the shear information indicates tissue characteristics or unreliable shear calculation.

20 Claims, 7 Drawing Sheets

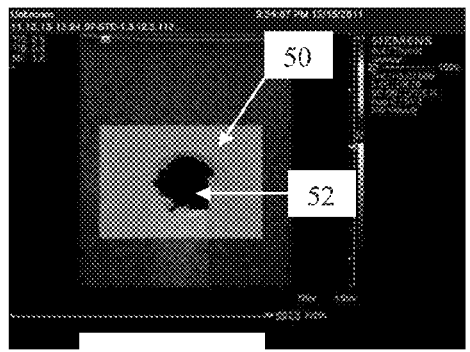 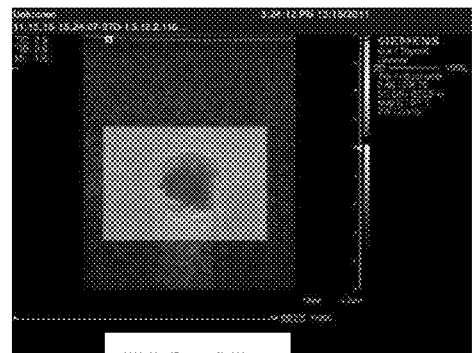
FIG. 3A  FIG. 3B
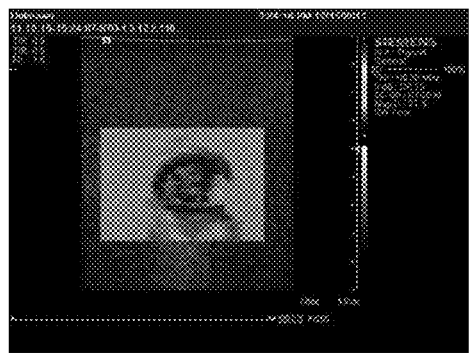 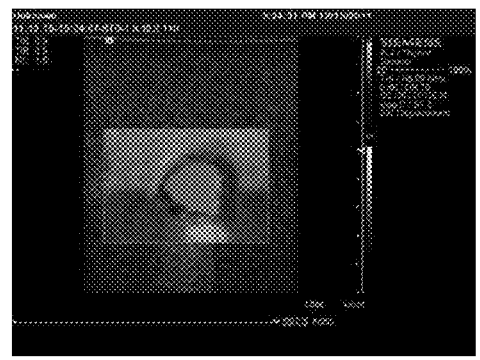
FIG. 3C  FIG. 3D
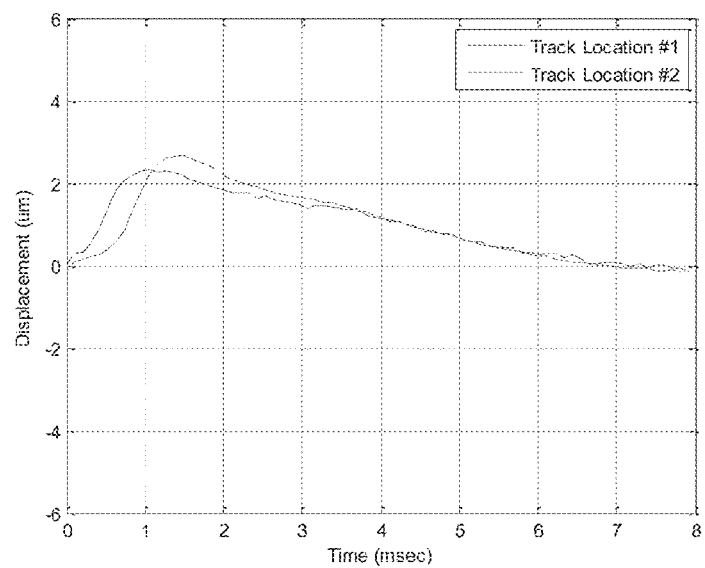
FIG. 4A

VISUALIZATION OF ASSOCIATED INFORMATION IN ULTRASOUND SHEAR WAVE IMAGING

RELATED APPLICATIONS

The present patent document claims the benefit of the filing dates under 35 U.S.C. §119(e) of Provisional U.S. Patent Application Ser. No. 61/599,785, filed Feb. 16, 2012, which is hereby incorporated by reference.

BACKGROUND

The present embodiments relate to ultrasound imaging. In particular, ultrasound shear wave imaging may be improved.

Shear wave velocity information may be useful for diagnosis. Shear wave information indicates a tissue characteristic in addition to acoustic impedance (e.g., B-mode) and Doppler (e.g., flow mode) imaging. However, the complexity of shear wave propagation in tissue may result in significant errors. For example, shear wave velocity may be less accurately determined for fluid or fluid tissue, resulting in seemingly arbitrary values.

BRIEF SUMMARY

By way of introduction, the preferred embodiments described below include methods, instructions, and systems for visualization of associated information in ultrasound shear wave imaging. More information than just a shear wave image is provided for diagnosis. Information about the quality or variables used to determine shear wave velocity is also displayed. This additional information may assist the user in determining whether the shear information indicates tissue characteristics or unreliable shear wave velocity calculation.

In a first aspect, a method is provided for visualization of associated information in ultrasound shear wave imaging. Displacements at locations within a patient are measured with ultrasound in response to one or more impulse excitations. Shear wave velocities are calculated as a function of the displacements for the locations. A quality of each of the displacements, a magnitude of each of the displacements, and a shear wave travel time are determined. A shear wave velocity image representing the locations is displayed. The shear wave velocity image is a function of the shear wave velocities. The quality, magnitude, and shear wave travel time for at least one of the locations are displayed at a substantially same time as the shear wave velocity image.

In a second aspect, a non-transitory computer readable storage medium has stored therein data representing instructions executable by a programmed processor for visualization of associated information in ultrasound shear wave imaging. The storage medium includes instructions for calculating a shear wave characteristic using at least one variable, generating an image of the shear wave characteristic, and displaying information derived from the variable in addition to the shear wave characteristic with the image.

In a third aspect, a system is provided for visualization of associated information in ultrasound shear wave imaging. A transducer is configured to transmit an acoustic impulse excitation into a patient and configured to scan with ultrasound a region of the patient. A receive beamformer is configured to generate data representing the region at different times after the acoustic impulse excitation. The data is generated from the scan with ultrasound. A processor is configured to estimate tissue displacement induced by the acoustic impulse excitation, generate a shear wave image as a function of the tissue displacement, and derive a quality of the tissue displacement. A display is configured to display the shear wave image and a representation of the quality of the tissue displacement.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIGS. 3A-D are example images for shear wave velocity, quality, displacement, and travel time for a phantom of a cyst;

FIG. 4A shows example displacement profiles for locations in soft tissue around a cyst.

DETAILED DESCRIPTION OF THE DRAWINGS AND PRESENTLY PREFERRED EMBODIMENTS

Solid tissue regions may allow for more accurate measurement of shear wave velocity. Other types of regions, such as fluid or fluid tissue, may be less accurately measured for shear wave velocity. A region of interest may include fluid (e.g., blood or urine), bone, and tissue. Tissue may include fluid like tissue (i.e., fluid tissue) or solid tissue. Solid tissues include muscle, fat, organs or other structure with a relatively more elastic character than fluid and bone. Cysts or other tissue structure may have a high fluid content, resulting in less reliable shear information.

When solid tissue and fluid tissue are excited by an impulse force, both tissues are displaced. The characteristic of the displacement profile over time may be different by the type of tissue. Displacement in solid tissue is governed by the shear wave equation, and displacement in fluid tissue is governed by Navier-Stokes equation. The resulting displacement profile in fluid tissue shows significant noise compared with the displacement profile in solid tissue. The signal-to-noise ratio (SNR) of echo signal also contributes to the SNR of the displacement profile.

To assist the user in distinguishing between poor shear detection and tissue characteristic, other information than the shear wave image is displayed. The other information may include a quality of the shear data, a magnitude of displacement associated with the shear data, and/or a travel time of the shear wave. This additional information may assist in diagnosis of tissue type or avoid reliance on unreliable shear data.

Figure 1:
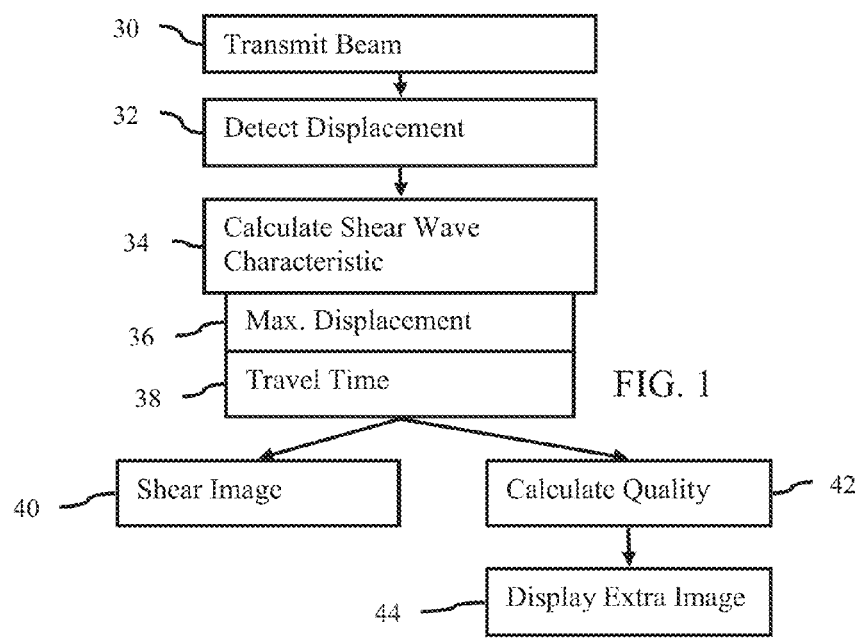
FIG. 1 is a flow chart diagram of one embodiment of a method for visualization of associated information in ultrasound shear wave imaging.

FIG. 1 shows a method for visualization of associated information in ultrasound shear wave imaging. The method is implemented by the system of FIG. 8 or a different system. Additional, different, or fewer acts may be provided. For example, acts 36, 38, and 42 represent examples. One, two, all three, or none of acts 36, 38, and 42 may be used. Other types of additional information may be used. As another example, act 30 is not performed. The stress for generating a shear wave may be generated without transmitting a beam, such as with a thumper. The acts are performed in the order described or shown, but may be performed in other orders.

The method is performed for one or more locations. In one embodiment, the method is performed for each of B-mode or scan sample locations in an entire field of view or just a region of interest. Less or more dense sampling may be used.

In act 30, an acoustic excitation is transmitted into a patient. The acoustic excitation acts as an impulse excitation for causing displacement. For example, a 400 cycle transmit waveform with power or peak amplitude levels similar or higher than B-mode transmissions for imaging tissue is transmitted as an acoustic beam. In one embodiment, the transmission is a shear wave generating sequence applied to the field of view. Any acoustic radiation force imaging (ARFI) or shear wave imaging sequence may be used.

The transmission is configured by power, amplitude, timing, or other characteristic to cause stress on tissue sufficient to displace the tissue at one or more locations. For example, a transmit focus of the beam is positioned near a bottom, center of the field of view or region of interest to cause displacement throughout the field of view. The transmission may be repeated for different sub-regions.

The excitation is transmitted from an ultrasound transducer. The excitation is acoustic energy. The acoustic energy is focused, resulting in a three-dimensional beam profile. The excitation is focused using a phased array and/or mechanical focus. The excitation may be unfocused in one dimension, such as the elevation dimension. The excitation is transmitted into tissue of a patient.

For shear wave imaging, the impulse excitation generates a shear wave at a spatial location. Where the excitation is sufficiently strong, a shear wave is generated. The shear wave propagates through tissue more slowly than the longitudinal wave along the acoustic wave emission direction. The shear wave propagates various directions, including a direction perpendicular to the direction of the applied stress. The displacement of the shear waves is greater at locations closer to the location at which the shear wave is generated.

In act 32, a displacement profile of response in the patient is detected. For example, the displacement profiles for two locations are demonstrated in FIG. 2. The excitation causes displacement of the tissue. A shear wave is generated and propagates from the focal region. As the shear wave travels through tissue, the tissue is displaced. Timing and/or lateral location are used to distinguish the shear wave from other generated waves. Longitudinal waves or other causes of displacement may be used instead of shear. The tissue is forced to move in the patient.

Figure 2:
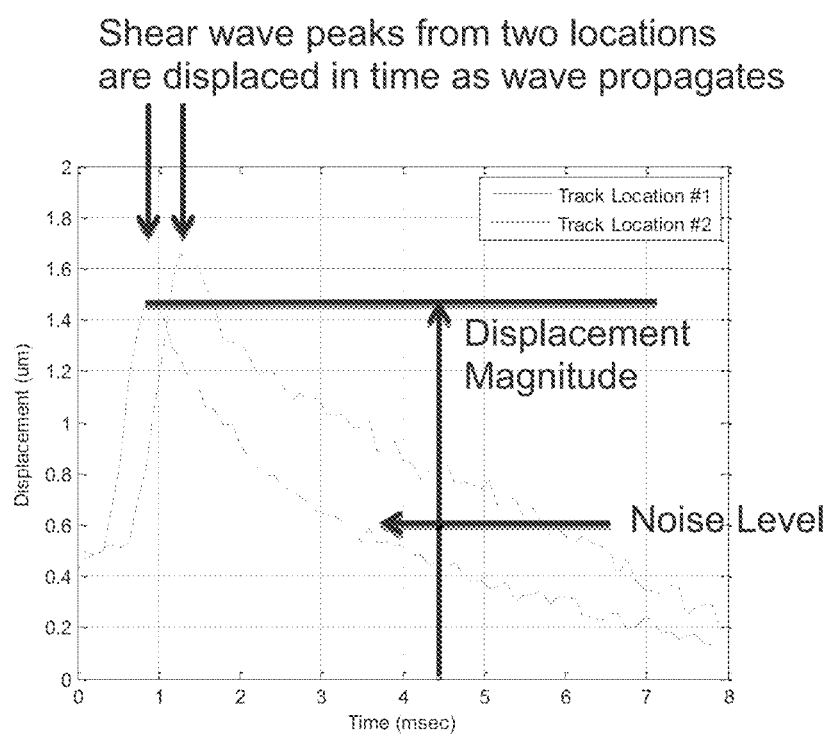
FIG. 2 is a graph showing two example displacements as a function of time.

The displacement caused by the force or stress is measured. The displacement is measured over time at one or more locations. The displacement measurement may begin before the stress or impulse ends, such as using a different frequency or coding. Alternatively, the displacement measurement begins after the impulse ends. Since the shear, longitudinal or other wave causing the displacement in tissue spaced from the point or region of stress takes time to travel, the displacement from a relaxed or partially stressed state to a maximum displacement and then to a relaxed state may be measured, as represented in FIG. 2. A temporal profile of displacement is determined. Alternatively, the displacement is measured only while the tissue is relaxing from the maximum.

The measurement is of the amount or magnitude of the displacement. The tissue is moved in any direction. The measurement may be along the direction of greatest movement. The magnitude of the motion vector is determined. Alternatively, the measurement is along a given direction, such as perpendicular to the scan line regardless of whether the tissue is displaced more or less in other directions.

The displacement is detected with ultrasound scanning. Ultrasound data is obtained. At least some of the ultrasound data is responsive to the shear wave. A region, such as a region of interest, entire field of view, or sub-region of interest, is scanned with ultrasound. The region is monitored to detect the shear wave. The region is any size, such as 6 mm in lateral and 10 mm in axial. For example, B-mode scans are performed to detect tissue displacement caused by the shear wave. Doppler, color flow, or other ultrasound mode may be used to monitor for the shear wave.

For a given time, ultrasound is transmitted to the tissue or region of interest. Any now known or later developed displacement imaging may be used. For example, pulses with 1-5 cycle durations are used with an intensity of less than 720 mW/cm$^2$. Pulses with other intensities may be used. The monitoring is performed for any number of scan lines. For example, four receive beams are formed in response to each transmission. After transmitting the excitation to generate the shear wave, B-mode transmissions are performed repetitively along a single scan line and receptions along four adjacent scan lines. In other embodiments, only a single receive beam or other numbers of receive beams are formed in response to each transmission. Additional transmit scan lines and corresponding receive line or lines may be used. Any number of repetitions may be used, such as about 120 times. Some of the ultrasound data, such as at the beginning or end of the repetitions, may not be responsive to the shear wave.

As the shear wave propagates through the scan lines, the B-mode intensity may vary due to displacement of the tissue. For the monitored scan lines, a sequence of data is provided representing a time profile of tissue motion resulting from the shear wave. Echoes or reflections from the transmission are received. The echoes are beamformed, and the beamformed data represents one or more locations. To detect the displacement, ultrasound energy is transmitted to the tissue undergoing displacement and reflections of the energy are received. Any transmission and reception sequence may be used.

By performing the transmitting and receiving multiple times, data representing a one, two, or three-dimensional region at different times is received. The transmission and reception are performed multiple times to determine change due to displacement. By repetitively scanning with ultrasound, the position of tissue at different times is determined.

The echoes are detected using B-mode or Doppler detection. The displacement is detected from the differences for each spatial location. For example, the velocity, variance, shift in intensity pattern (e.g., speckle tracking), or other information is detected from the received data as the displacement.

In one embodiment using B-mode data, the data from different scans is correlated as a function of time. Any elasticity detection may be used. For each depth or spatial location, a correlation over a plurality of depths or spatial locations (e.g., kernel of 64 depths with the center depth being the point for which the profile is calculated) is performed. For example, a current set of data is correlated multiple times with a reference set of data. The location of a sub-set of data centered at a given location in the reference set is identified in the current set. Different relative translations and/or rotations between the two data sets are performed.

The reference is a first set of data or data from another scan. The same reference is used for the entire displacement detection, or the reference data changes in an ongoing or moving window.

The correlation is one, two or three-dimensional. For example, correlation along a scan line away and toward the transducer or along a line perpendicular to the scan line is used. As another example, the translation is along two axes with or without rotation. In yet another example, the translation is along three axes with or without rotation about three or fewer axes. The level of similarity or correlation of the data at each of the different offset positions is calculated. The translation and/or rotation with a greatest correlation represents the motion vector or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

FIG. 2 shows two example displacement profiles. The magnitude in distance of the motion vector over time from the reference data is shown. The period of analysis is over about 8 milliseconds, but may be longer or shorter. Other displacement profiles are possible.

Referring again to FIG. 1, one or more shear wave characteristics are calculated in act 34. Shear wave characteristics may include velocity of the shear wave. The shear wave characteristic may be a modulus or other characteristic of the tissue derived from the shear wave.

To determine the shear wave characteristic, one or more variables are used. For example, shear wave velocity is detected from the displacement. The displacement is a variable. Where a displacement over time is determined, a maximum displacement or other magnitude of displacement is calculated. The magnitude of displacement is a variable. The displacement and distance may be used to determine a travel time of the shear wave from a focal region to the location being monitored. The travel time is a variable. The distance is a variable. Other variables may be used, such as intensity of acoustic return used to determine the displacement.

Other values may be derived from the variable than the shear characteristic. For example, a quality is determined from the displacement profile, magnitude, and/or characteristic of the ultrasound data used to determine the displacement.

The magnitude of displacement caused by the shear wave is determined. The displacement may be higher in soft tissue and lower in stiff or hard tissue. The magnitude may be from a given time based on a distance from the focal region to the monitored location. Alternatively, the magnitude may be derived from the displacement profile over time, such as identifying a maximum displacement in act 36. The maximum displacement is determined for the magnitude of the displacement. The maximum displacement is calculated from the displacement profile. The peak or highest amount of motion or magnitude of shift by the tissue along a line, within a plane, or within a volume is calculated. The smoothed or filtered displacement curve is used for the maximum calculation. In other embodiments, the raw or unfiltered displacement curve may be used. The maximum value over the entire or portion of the profile is identified or determined. In the example of FIG. 2, the maximum displacement of 1.45 micrometers occurs at about 0.9 milliseconds for one location, and the maximum displacement of 1.65 micrometers occurs at about 1.2 milliseconds for the other location.

The temporal profile for a given location indicates detection of the shear wave. The profile is examined for a non-noise or single instance of variation. A peak in the profile, with or without temporal low pass filtering, indicates the passing of the shear wave front. The greatest displacement is selected, but the average, initial non-noise displacement, or other displacement statistic may be used to indicate the passing.

In act 38, a shear wave travel time is calculated as a function of the displacements. The time or duration for the shear wave to travel from the origin (e.g., transmit focal region) to the location is determined. The maximum displacement or other part of the displacement profile indicates the time of arrival of the shear wave. Using the timing from generation of the shear wave to arrival, the travel time is calculated. The time is known from the relative time between generation and detection of the shear wave. The travel time may be non-linear.

The velocity of the shear wave is calculated from the timing information. The travel time is the inverse of the velocity. Using the distance and the travel time, the velocity is calculated. The distance is known from the scan line spacing (i.e., the transmit beam position for generating the shear wave and the receive beam position for detecting the shear wave).

Other techniques may be used to detect the peak in the profile and corresponding time and velocity. For example, a regression is applied. Since the shear wave velocity is linear, a robust linear regression with automated outlier detection may indicate the shear wave velocity. The ultrasound data for all of the sample points in the region of interest is plotted for distance as a function of time or by time and distance. The linear regression is applied to the plot or data, providing a line fit to the data. The slope of the line indicates the shear wave velocity.

In act 42, a quality is determined. The quality is calculated from the ultrasound data used to determine displacement, from the displacement profile, from the magnitude, and/or from any other source associated with detecting the shear and calculating the shear characteristic. In one example embodiment, the quality is calculated as a function of the magnitude, the signal-to-noise ratio (SNR) of the displacement over time, and the signal-to-noise ratio of the ultrasound signal. Any function combining these inputs may be used.

The SNR of the displacement profile is determined. The SNR of the displacement over or as a function of time is determined by identifying noise from the profile. Noise may be identified in any way, such as selecting high frequency components of the profile. A Fourier transform may be used to determine the high frequency noise.

In one embodiment for identifying the noise, the displacement profile is filtered. A low pass filter, such as a Butterworth filter, is applied to the profile (i.e., temporal filtering). The filter is an infinite impulse response (IIR) filter or a finite impulse response (FIR) filter. The filtered displacement over time is subtracted from the displacement over time prior to filtering. The difference represents the noise.

In another embodiment, the noise and signal levels are calculated from the displacement profile. The noise information is quantified. The root mean square (RMS) of the noise signal is calculated to represent the noise level. Other calculations may be used, such as an average of the absolute values of the peaks. The signal level is calculated. In one embodiment, the signal level is represented by the area under the filtered displacement profile. The integral of the filtered displacement is calculated. Other signal level measurements may be used. The SNR is provided by dividing the signal (e.g., integral of the filtered displacement) by the noise (e.g., RMS of the noise). Other functions may be used, including other variables.

The SNR of the ultrasound signal may be determined for quality. The ultrasound signal's SNR may be calculated as ratio between the receive signal intensity with and without transmitting to scan. Other approaches for determining signal SNR may be used.

Other possible indicators of quality include a level of correlation. A de-correlation coefficient may be calculated as 1 minus the normalized correlation coefficient of the echo signals detected before and after the impulse excitation.

Another possible indicator is a statistic of the ultrasound data. For example, the mean of the B-mode information for a location over the same period used for the displacement profile is calculated. Higher order statistics may be calculated instead or in addition. Any statistic or other parameter may be used for indicating quality. The statistic may be spatial and/or temporal.

One parameter may be used for the quality. For example, a low magnitude indicates poor quality while a high magnitude indicates better quality. As another example, low SNR of the ultrasound data or the displacement profile indicates better quality shear information.

In one embodiment, multiple parameters are used for quality, such as using the displacement SNR and magnitude, with or without data SNR. If the maximum displacement is low, there may be low quality. For low maximum displacement, the quality is assigned as low. For lower SNR and higher displacement, the quality may be assigned as low or a medium quality. For other combinations of the two parameters, the quality is assigned as good. Other functions may be used. For example, a threshold distinguishes between good and bad quality for each of SNR and magnitude of displacement. If both are good, the quality is good. If both are bad, the quality is bad. If a combination of good and bad parameters is provided, then the quality is bad or medium. Any number of quality distinctions may be used, such as binary, three levels, or more levels.

The quality function is based on experiments, a mathematical function, statistics, or other information. For example, fuzzy logic is used to determine quality. In this method, a membership function for each parameter is empirically defined (e.g. SNR, maximum displacement), and the outputs of each membership function given the input parameters at a location are summed to generate the likelihood of quality. The maximum value of the sum corresponds to the quality to be assigned. As another example, machine learning from a collection of training samples or data with known ground truth regarding the quality is used to determine statistics or a matrix function for quality. A probability function indicates the likelihood of each quality for a given location, and the quality with the highest probability is selected. The quality determination is performed using a lookup table, fuzzy logic function, programmed function, or matrix function.

The quality for each location relies on data for that location and not data for other locations. In alternative embodiments, spatial filtering or information from adjacent locations may be used for classifying quality for a given location.

Figure 4B:
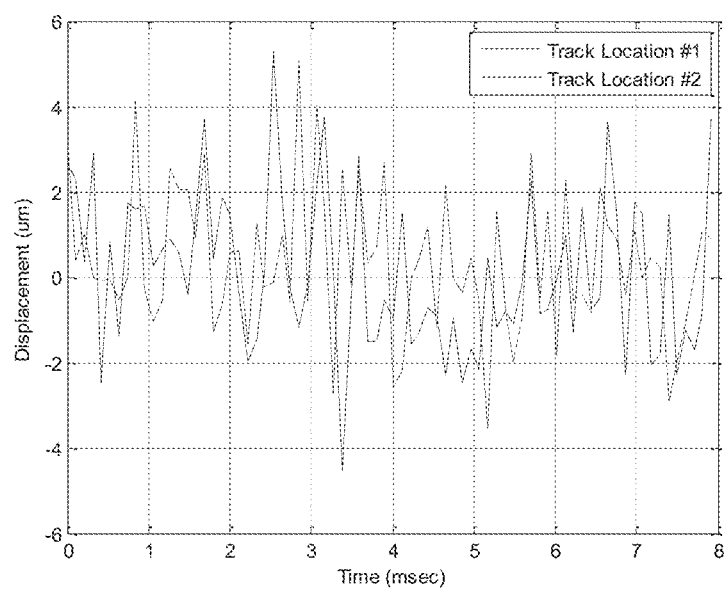
FIG. 4B shows example displacement profiles for locations within the cyst.
Figure 5A:
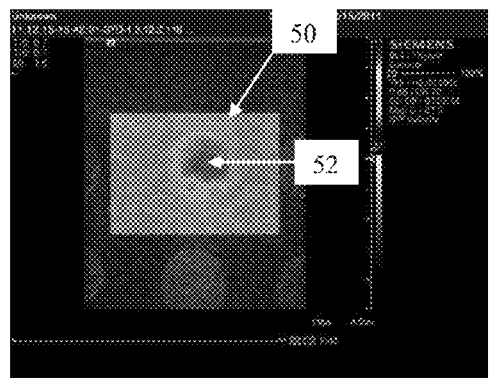
FIG. 5A-D are example images for shear wave velocity, quality, displacement, and travel time for a phantom of a hard inclusion.
Figure 5B:
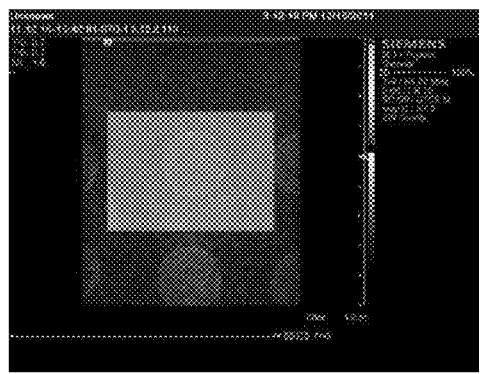
Figure 5C:
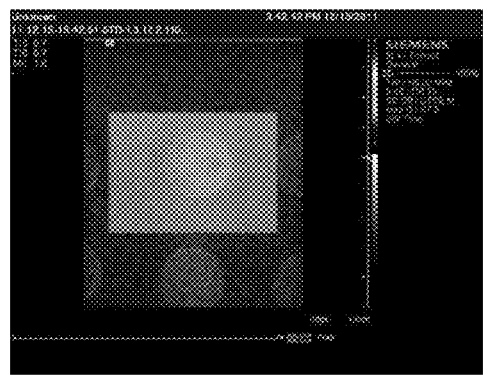
Figure 6A:
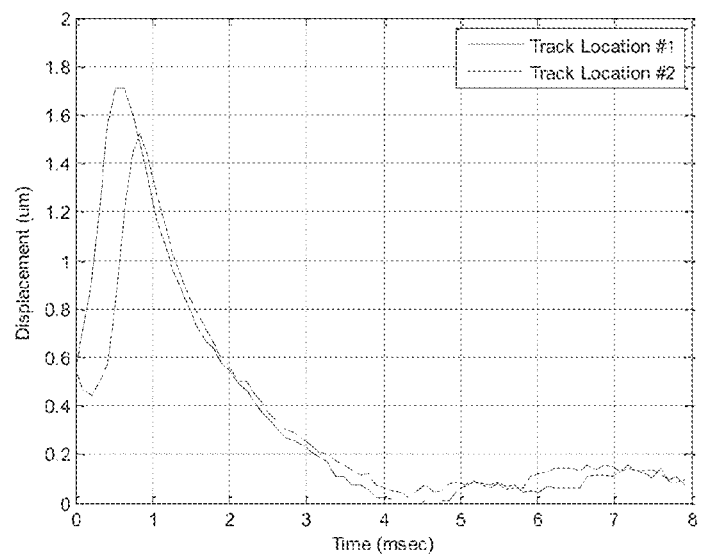
FIG. 6A shows example displacement profiles for locations in soft tissue around the hard inclusion.
Figure 6B:
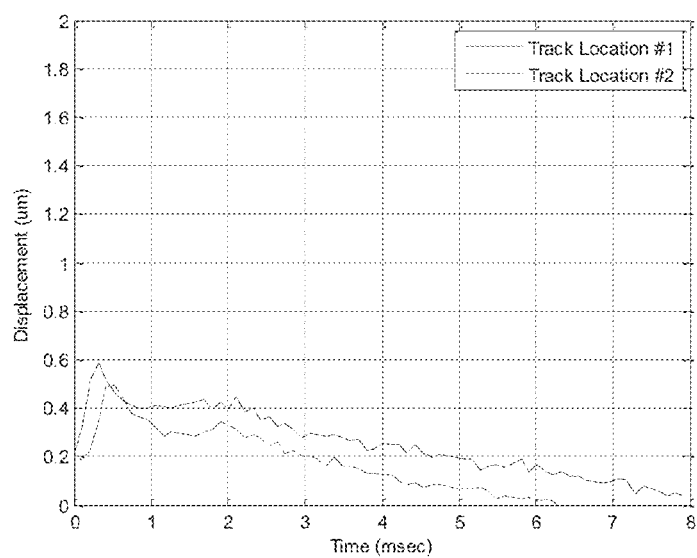
FIG. 6B shows example displacement profiles for locations within the hard inclusion.

FIGS. 3B and 5B represent quality in two examples. The quality is determined over a range of values, such as mapping quality to 64 different values. FIGS. 3A and 5A are shear wave velocity images for a cyst with a fluid tissue center and a hard inclusion, respectively. An outer region 50 includes soft tissue. FIGS. 4A and 6A show the displacement profiles for two locations in the outer region 50. The inner region 52 of FIG. 3A includes fluid tissue. The black of the inner region 52 may indicate no shear wave being detected. The inner region 52 of FIG. 5A includes hard tissue. FIGS. 4B and 6B show the displacement profiles for two locations in the inner region 50 for the cyst and the hard inclusion, respectively. The displacement of FIG. 4B is noisy and has unusually large displacement. The quality is mapped to a low level. The displacement of FIG. 6B has low magnitude due to the hard tissue attenuating the shear waves, but is not relatively noisy. The non-noisy displacement with lower magnitude is mapped to a mid range of quality.

Shear wave velocity and/or quality are calculated for the different spatial locations of the tissue. FIGS. 3A and 5A show a rectangular region of interest in which shear wave velocity is calculated. The displacement profile and characteristics for the displacement profile are determined for each location in the region. The repetition uses the same or different transmission in act 30. Where the region of interest is sufficiently small, one impulse is used. The displacement at different locations is determined using a window centered on each of the locations. For each location, the window or kernel is centered over the location. The data representing spatial locations within the window is used for correlation. Displacement is separately determined for each location. In other embodiments, the transmission act 30 is repeated. Displacements for one, some or a subset of the region of interest are determined in response to each transmission of act 30.

In a 6 mm×10 mm region of interest example, 36 receive scan lines may be provided. At four receive beams per transmit beam, the process is repeated for different lateral spacing nine times. For each receive beam location, a time profile of motion information is provided, represented by the ultrasound data. Transmissions along different scan lines to monitor a same shear wave are avoided during formation of the temporal profile to provide higher temporal resolution, but interleaved or shifting scanning positions may be provided. Narrower regions of interest may allow for displacement detection with fewer repetitions of transmitting the excitation waveform of act 30. Depending on the number of receive beams that may be formed and the sample density, none, one, or more repetitions may be used.

The discussion above is for one depth. The sampling may be arranged to provide one gate covering the entire axial extent of the region of interest. In another embodiment, samples are obtained at multiple depths for each receive beam. A separate time profile is provided for each axial depth as well as lateral location. Any number of depths may be used, such as about 200 for 5 mm or 400 for 10 mm.

Full sampling, such as sampling displacement on every B-mode sample location, may be used. Greater or lesser (e.g., sparse) sampling of displacement relative to the B-mode scan grid may be used.

In act 40, an image of the shear wave characteristic is generated. Shear wave imaging is performed. The shear wave velocity, modulus or other information determined from tissue reaction to a shear wave is displayed. Any shear imaging may be used. The displayed image represents shear wave information for the region of interest or the entire imaging region. For example, where the velocity values are determined for all of the grid points in a region of interest or field of view, the pixels of the display represent the shear wave velocities for that region. The display grid may be different from the scan grid and/or grid for which displacements are calculated.

The shear wave information is used for a color overlay or other modulation of display values. Color, brightness, luminance, hue, or other display characteristic is modulated as a function of the shear wave characteristic, such as the shear wave velocity. The image represents a two- or three-dimensional region of locations. The shear data is in a display format or may be scan converted into a display format. The shear data is color or gray scale data, but may be data prior to mapping with gray scale or color scale. The information may be mapped linearly or non-linearly to the display values.

The image may include other data. For example, shear wave information is displayed over or with B-mode information. B-mode or other data representing tissue, fluid, or contrast agents in the same region may be included, such as displaying B-mode data for any locations with shear wave velocity below a threshold or with poor quality. The other data assists the user in determining the location of the shear information. In other embodiments, the shear wave characteristic is displayed as an image without other data.

In act 44, other information is displayed. The other information is or is derived from one or more variables used to calculate the shear wave characteristic of the shear wave image of act 40. For example, the shear wave velocity in a two-dimensional region of interest is displayed in act 40. In act 44, the displacement, the maximum displacement, the time of travel, and/or the quality of act 42 is displayed. The quality may be derived from one or more variables, such as the quality being based on the displacement (e.g., maximum and signal-to-noise ratio).

The additional information is displayed for one or more of the variables or derivations from the variables. In one embodiment, additional information is displayed for two, three, or more variables or derivations of the variables. For example, the quality, maximum displacement, and time of travel information are displayed.

The shear wave characteristic and the additional information are displayed substantially simultaneously. The "substantially" accounts for visual perception of the view. Displaying two images sequentially with sufficient frequency may allow the viewer to perceive the images as being displayed at a same time.

Any format for substantially simultaneous display may be used. In one example, the shear wave image of act 40 is a two-dimensional image. The additional information is text, a graph, two-dimensional image, or other indicator of the values of the information.

Figure 7:
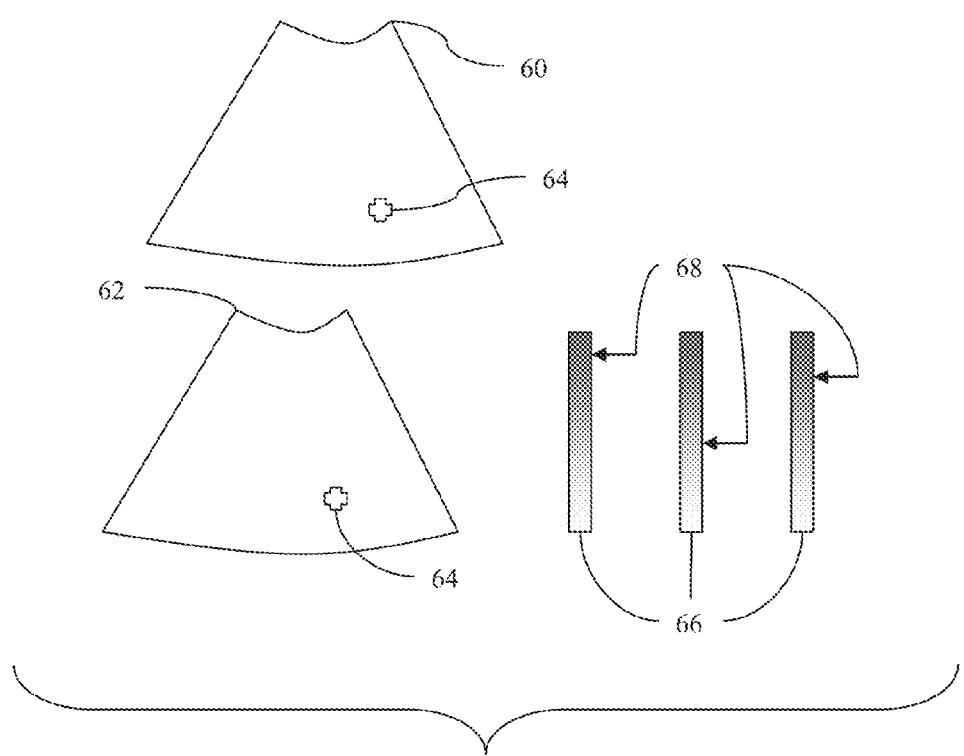
FIG. 7 is an alternative embodiment of a display of shear and other information.

FIG. 7 shows one example format. A B-mode image 60 is displayed on the screen. The shear wave image 62 is also displayed on the screen. In other embodiments, the shear wave information is a color overlay on the B-mode image 60 rather than being a separate image or displayed without the B-mode image 60. A cursor 64 or other location selection is positioned relative to one or both of the images 60, 62. The cursor indicates selection of a location associated with shear wave velocity information. For example, the user selects a pixel associated with an interior region of a lesion, cyst, inclusion, or other structure.

The other information is represented by one or more scales 66. Each scale is a range of values for a given type of information. For example, one scale 66 is for time of travel, another scale 66 is for maximum displacement, and another scale 66 is for quality. More or fewer scales may be provided. Each scale 66 is a range of values indicated by numbers, gray level, or color. The range is appropriate for the type of information represented by the scale.

An indicator 68 shows values associated with the cursor 64 or other selected location. The indicator 68 shows the point within the range of the scale 66 for a given location. By selecting a location or positioning the cursor, the indicator 68 for each scale 66 is positioned as appropriate. The quality, maximum displacement, time of travel, or other information for the location is used to determine the position of the indicator 68. The indicator 68 shows the value for the information associated with the selected location.

As the location changes or other locations are selected, the indictor 68 is positioned as appropriate along the scale 66. By positioning the cursor 64 or selecting different locations, the user is provided with information in addition to the shear wave characteristic. The additional information, such as the quality, may be used to assist in diagnosis. In alternative embodiments, text is displayed instead of the scales 66 and indicators 68.

FIGS. 3A-D and 5A-D show another example format. The variable or variable derived information is displayed as a two-dimensional image. With the same or different resolution, the additional information for the same region as the shear wave image is displayed for locations distributed over two spatial dimensions.

The images are displayed substantially simultaneously. For example, a quad-screen display is used. The shear wave image (e.g., shear wave velocity in FIGS. 3A and 5A) is displayed in one area of the screen. The additional information is displayed in one or more other areas of the screen. In the examples of FIGS. 3A-D and 5A-D, two-dimensional images for quality (FIGS. 3B and 5B), time of travel (FIGS. 3C and 5C), and maximum displacement (FIGS. 3D and 5D) are displayed.

Figure 5D:
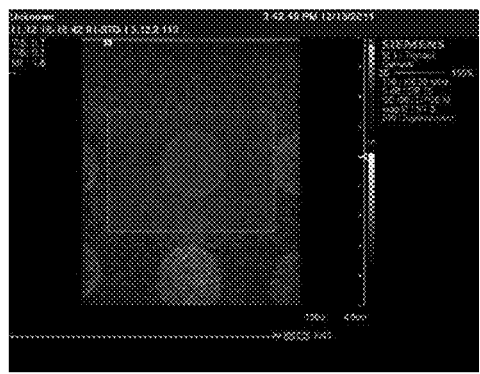

The user may view the different images on the screen for diagnosis. For example, the low quality at the center of the cyst shown in FIG. 3B explains the black region in the velocity of FIG. 3A. The corresponding variance in the time of travel and the ring appearance in the displacement indicate fluid tissue. Conversely, FIG. 5B shows good quality in the inner portion, as well as consistent time of travel (FIG. 5C) and displacement (FIG. 5D). The additional information helps the user diagnosis the region as a hard inclusion.

Figure 8:
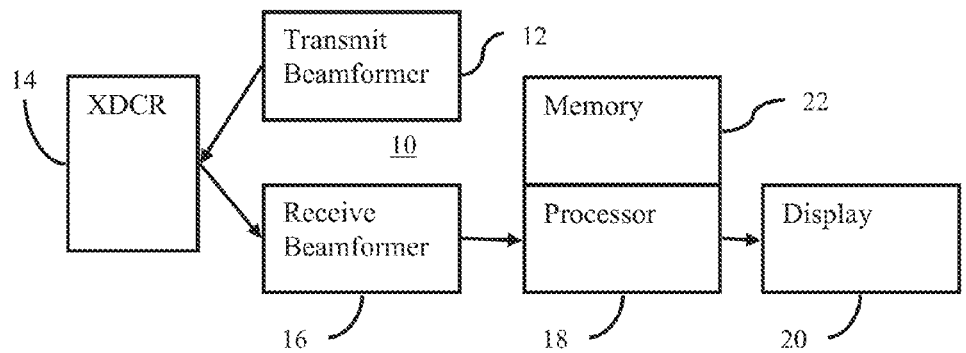
FIG. 8 is a block diagram of one embodiment of a system for visualization of associated information in ultrasound shear wave imaging.

FIG. 8 shows one embodiment of a system 10 for visualization of associated information in ultrasound shear wave imaging. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system.

The system 10 is a medical diagnostic ultrasound imaging system. In alternative embodiments, the system 10 is a personal computer, workstation, PACS station, or other arrangement at a same location or distributed over a network for real-time or post acquisition imaging.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated electrical waveforms, one or more beams are formed. A sequence of transmit beams are generated to scan a two or three-dimensional region. Sector, Vector®, linear, or other scan formats may be used. The same region is scanned multiple times. For flow or Doppler imaging and for shear imaging, a sequence of scans along the same line or lines is used. In Doppler imaging, the sequence may include multiple beams along a same scan line before scanning an adjacent scan line. For shear imaging, scan or frame interleaving may be used (i.e., scan the entire region before scanning again). Line or group of line interleaving may be used. In alternative embodiments, the transmit beamformer 12 generates a plane wave or diverging wave for more rapid scanning.

The same transmit beamformer 12 generates impulse excitations or electrical waveforms for generating acoustic energy to cause displacement. In alternative embodiments, a different transmit beamformer is provided for generating the impulse excitation. The transmit beamformer 12 causes the transducer 14 to generate pushing pulses or acoustic radiation force pulses.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event provides a pulse of ultrasound energy for displacing the tissue. The pulse is an impulse excitation or tracking pulse. Impulse excitation includes waveforms with many cycles (e.g., 500 cycles) but that occurs in a relatively short time to cause tissue displacement over a longer time. A tracking pulse may be B-mode transmission, such as using 1-5 cycles. The tracking pulses are used to scan a region of a patient.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging or tracking transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

In coordination with the transmit beamformer 12, the receive beamformer 16 generates data representing the region at different times. After the acoustic impulse excitation, the receive beamformer 16 generates beams representing different lines or locations at different times. By scanning the region of interest with ultrasound, data (e.g., beamformed samples) is generated. By repeating the scanning, ultrasound data representing the region at different times after the impulse excitation is acquired.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for displacement. Alternatively, the B-mode data is also used to determine displacement. As another example, data for displacement-based classification and shear imaging is performed with a series of shared scans and B-mode or Doppler scanning is performed separately or using some of the same data.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information for display from beamformed ultrasound samples. In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacement, identifying magnitude of displacement, calculating travel time, and calculating shear wave velocity. For example, the separate processor is configured by hardware and/or software to perform any combination of one or more of the acts shown in FIG. 1.

The processor 18 is configured to estimate tissue displacement induced by the acoustic impulse excitation. Using correlation, tracking, motion detection, or other displacement measuring, the amount of shift in position of the tissue is estimated. The estimation is performed multiple times through a period, such as from prior to the tissue moving due to the impulse to after the tissue has mostly or completely returned to a relaxed state (e.g., recovered from the stress caused by the impulse excitation).

The processor 18 is configured to derive at least one parameter describing a characteristic of a profile of the tissue displacement. For example, the signal-to-noise ratio of the displacement profile is derived. As another example, the maximum displacement of the displacement profile is derived. The processor 18 may calculate other parameters, such as a statistic or signal-to-noise ratio of the data in time, space, or time and space. For example, an average B-mode or acoustic impedance value over time and/or space for each location is calculated.

The processor 18 is configured to calculate a shear wave characteristic, such as the shear wave velocity or modulus. The maximum or other displacement is used to determine a travel time of the shear wave. The velocity is calculated using distance and the travel time. Velocity is determined for any number of locations.

The processor 18 may be configured to determine a quality of the shear wave imaging in the region. Tissue may be fluid tissue or solid tissue. The quality may indicate to what extent the shear wave information should be trusted or is accurate. The quality is based on at least one parameter. For example, the quality is based on values for one or more characteristics of the displacement profile. The signal-to-noise ratio and the maximum displacement are two such characteristics. Other information, such as a statistic of other data, may be used in the quality parameter.

The processor 18 implements fuzzy logic, a probability function, lookup table, or other process. The input features (e.g., characteristics of the displacement profile) are applied to the process to determine the quality at different locations.

The processor 18 is configured to generate one or more images. For example, a shear wave velocity image is generated. The shear wave velocity image is presented as an overlay or region of interest within a B-mode image, such as shown in FIGS. 3A and 5A. The shear wave velocity modulates the color at locations in the region of interest. Where the shear wave velocity is below a threshold or of a sufficiently poor quality, B-mode information may be displayed without modulation by the shear wave velocity.

Other images may be displayed sequentially or substantially simultaneously. For example, a quality, maximum displacement, and/or travel time images are displayed at a same time as the shear wave velocity. Each is generated as a color overlay in the region of interest in B-mode images, such as shown in FIGS. 3B-D and FIGS. 5B-D.

The processor 18 may be configured to generate other displays. For example, the shear wave velocity image is displayed next to a graph, text, or graphical indicators of values of the quality, displacement, travel time, or other variable related to the shear wave measurements. FIG. 7 shows an example. The information in addition to the shear wave velocity is presented for one or more locations of the region of interest without being in a separate two or three-dimensional representation.

The processor 18 operates pursuant to instructions stored in the memory 22 or another memory for visualization of associated information in ultrasound shear wave imaging. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The two dimensional images represent spatial distribution in an area. The three-dimensional representations are rendered from data representing spatial distribution in a volume. The display 20 is configured by the processor 18 or other device by input of the signals to be displayed as an image. The display 20 displays an image representing shear for different locations in a region of interest or an entire image. The display 20 displays information about one or more variables used to determine or related shear wave velocity or modulus, such as displacement, maximum displacement, roll-off of displacement, signal-to-noise ratio of displacement, signal-to-noise ratio of data used to derive displacement, other displacement profile statistic, travel time, variance in travel time, or quality. The additional information may assist in diagnosis or confidence in shear information.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for visualization of associated information in ultrasound shear wave imaging, the method comprising:
    measuring, with ultrasound, displacements at locations within a patient in response to one or more impulse excitations;
    calculating shear wave velocities as a function of the displacements for the locations;
    determining a quality of each of the displacements;
    determining a magnitude of each of the displacements;
    calculating a shear wave travel time for each of the locations as a function of the displacements, wherein the shear wave travel time is the time it takes the shear wave to travel from a focal region of the one or more impulse excitations to a respective location;
    displaying a shear wave velocity image representing the locations, the shear wave velocity image being a function of the shear wave velocities; and
    displaying the quality, magnitude, and shear wave travel time for at least one of the locations at a substantially same time as the shear wave velocity image.

2. The method of claim 1 further comprising:
    transmitting an acoustic excitation into a patient, the impulse excitation comprising the acoustic excitation;

wherein measuring the displacements comprises repetitively scanning the locations with the ultrasound.

3. The method of claim 1 wherein calculating the shear wave velocities comprises determining a maximum of the displacements over time for each of the locations.

4. The method of claim 1 wherein determining the quality comprises determining a signal-to-noise ratio of the displacement over time.

5. The method of claim 4 wherein determining the signal-to-noise ratio comprises:
filtering the displacement over time;
subtracting the filtered displacement over time from the displacement over time;
calculating a root mean square of a result of the subtracting; and
dividing an integral of the filtered displacement by the root mean square, a result of the dividing comprising the signal-to-noise ratio.

6. The method of claim 4 wherein determining the quality further comprises:
determining a signal-to-noise ratio of an ultrasound signal; and
determining the quality as a function of the magnitude, the signal-to-noise ratio of the displacement over time, and the signal-to-noise ratio of the ultrasound signal.

7. The method of claim 1 wherein determining the magnitude comprises determining a maximum displacement over time for each location.

8. The method of claim 1 wherein calculating the shear wave travel time comprises calculating a duration for the shear wave to travel from an origin to the corresponding location, a time that the shear wave reaches the corresponding location being based on the displacements as a function of time.

9. The method of claim 1 wherein displaying the shear wave velocity image comprises displaying the shear wave velocity image as a two-dimensional image representing the shear wave velocities at the locations.

10. The method of claim 1 wherein displaying the quality, magnitude, and shear wave travel time comprises:
displaying a quality image of the qualities at the locations;
displaying a magnitude image of the magnitudes at the locations; and
displaying a travel time image of the shear wave travel times at the locations.

11. The method of claim 1 wherein displaying the quality, magnitude, and shear wave travel time comprises displaying for a cursor indicated location of the shear wave velocity image.

12. The method of claim 1 wherein displaying the quality, magnitude, and shear wave travel time comprises displaying a range and indicating a point on the range for each of the quality, magnitude, and shear wave travel time.

13. In a non-transitory computer readable storage medium having stored therein data representing instructions executable by a programmed processor for visualization of associated information in ultrasound shear wave imaging, the storage medium comprising instructions for:
calculating a shear wave characteristic using at least one variable;
generating an image of the shear wave characteristic; and
displaying information derived from the variable in addition to the shear wave characteristic with the image,
wherein calculating the shear wave characteristic comprises calculating as a function of a displacement as the variable, and wherein displaying comprises displaying a quality of the displacement as the information, the quality determined as a function of a magnitude of the displacement, a signal-to-noise ratio of the displacement over time, and a signal-to-noise ratio of an ultrasound signal.

14. The non-transitory computer readable storage medium of claim 13 wherein calculating the shear wave characteristic further comprises calculating as a function of a magnitude of displacement as the variable, and wherein displaying further comprises displaying the magnitude of displacement as the information.

15. The non-transitory computer readable storage medium of claim 13 wherein calculating the shear wave characteristic further comprises calculating as a function of a shear wave travel time as the variable, and wherein displaying further comprises displaying the shear wave travel time as the information.

16. The non-transitory computer readable storage medium of claim 13 wherein displaying further comprises displaying an additional image of the information distributed over at least two spatial dimensions, the additional image displayed substantially simultaneously with the image of the shear wave characteristic.

17. The non-transitory computer readable storage medium of claim 13 wherein displaying comprises displaying an indicator on a range, the indicator associated with a value of the information within the range.

18. A system for visualization of associated information in ultrasound shear wave imaging, the system comprising:
a transducer configured to transmit an acoustic impulse excitation into a patient and configured to scan with ultrasound a region of the patient;
a receive beamformer configured to generate data representing the region at different times after the acoustic impulse excitation, the data generated from the scan with ultrasound;
a processor configured to estimate tissue displacement induced by the acoustic impulse excitation, generate a shear wave image as a function of the tissue displacement, and derive a quality of the tissue displacement; and
a display configured to substantially simultaneously display the shear wave image and a representation of the quality of the tissue displacement.

19. The system of claim 18 wherein the processor is configured to derive the quality as a function of a signal-to-noise ratio of the tissue displacement over time and a maximum displacement of the tissue displacement over time.

20. The system of claim 18 wherein the processor is configured
generate the shear wave image as a shear wave velocity image where the representation is a two-dimensional image of the quality, text, or an indicator on a range of values of the quality.

* * * * *